US005464406A

United States Patent [19]
Ritter et al.

[11] Patent Number: 5,464,406
[45] Date of Patent: Nov. 7, 1995

[54] INSTRUMENTATION FOR REVISION SURGERY

[76] Inventors: Merrill A. Ritter, 9147 W. 82nd St., Indianapolis, Ind. 46278; John M. McDaniel, 2115 N. Industrial Dr., Bloomington, Ind. 47404; David R. Brown, 3997 E. Lakeview Trail, Leesburg, Ind. 46538

[21] Appl. No.: 988,229

[22] Filed: Dec. 9, 1992

[51] Int. Cl.[6] .................................................. A61F 5/00
[52] U.S. Cl. .................................. 606/86; 606/62; 606/87
[58] Field of Search .................................. 606/62–68, 86, 606/87, 88

[56]  References Cited

U.S. PATENT DOCUMENTS

| | | | |
|---|---|---|---|
| 4,567,885 | 2/1986 | Androphy | 606/88 |
| 4,703,751 | 11/1987 | Pohl | 606/87 |
| 4,875,475 | 10/1989 | Comte | 606/64 |
| 4,935,023 | 6/1990 | Whiteside | 606/88 |
| 4,938,762 | 7/1990 | Wehrli | 606/88 |
| 4,952,213 | 8/1990 | Bowman | 606/88 |
| 5,037,423 | 8/1991 | Kenna | 606/87 |
| 5,108,396 | 4/1992 | Lackey | 606/87 |
| 5,228,459 | 7/1993 | Caspari | 606/86 |

OTHER PUBLICATIONS

"The Continuum Knee System Surgical Technique", Techmedica Sales Brohcure, 1990.

Primary Examiner—Michael A. Brown
Attorney, Agent, or Firm—Harness, Dickey & Pierce

[57]  ABSTRACT

A set of surgical instruments for use in shaping a bone so as to receive one component of a joint prosthesis. The set of surgical instruments includes at least one resection guide which is operable to be used during resection of the bone. In addition, the set of surgical instruments includes a support member for adjustably positioning the resection guide in response to the provisional placement of the component of the joint prosthesis.

19 Claims, 11 Drawing Sheets

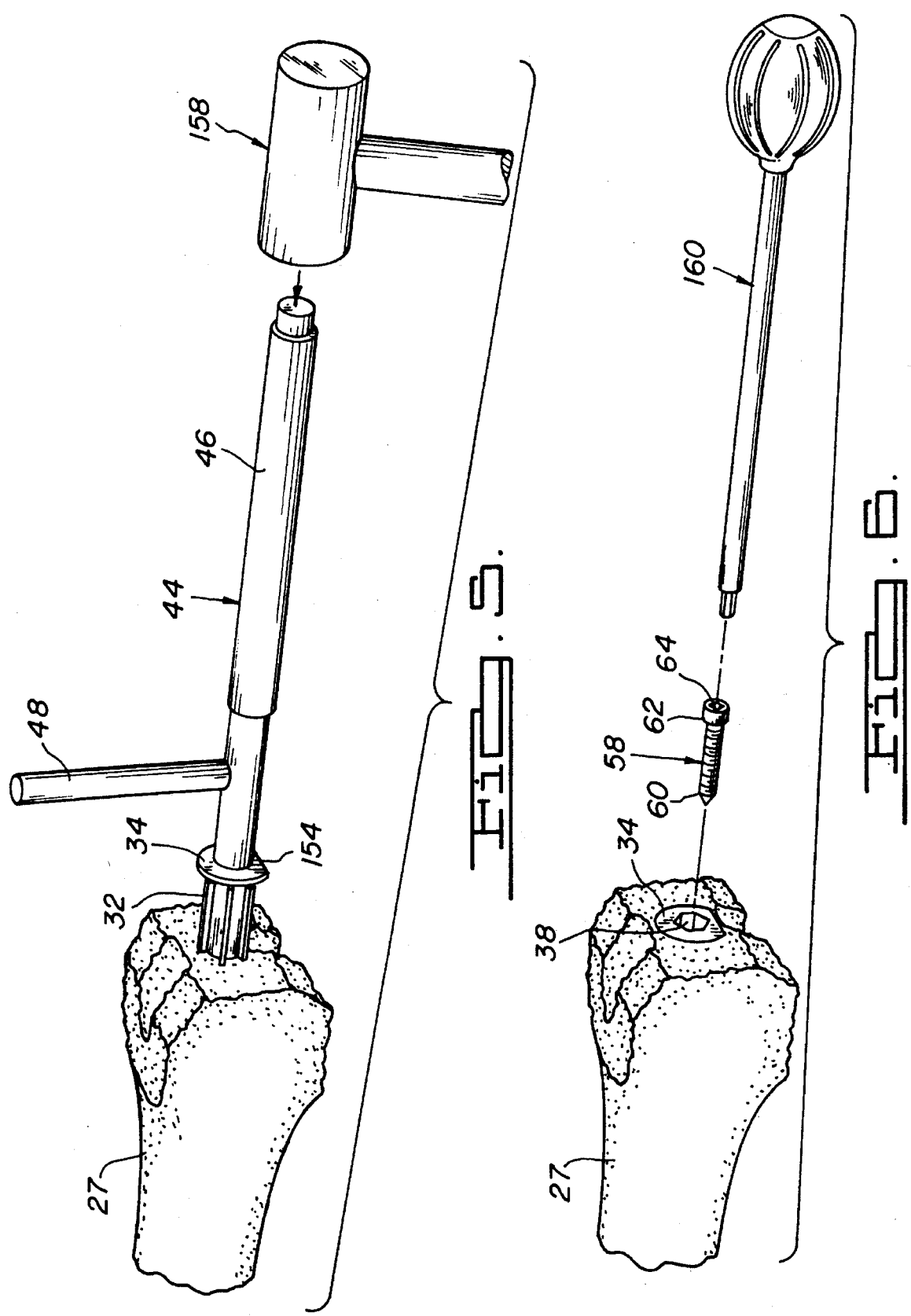

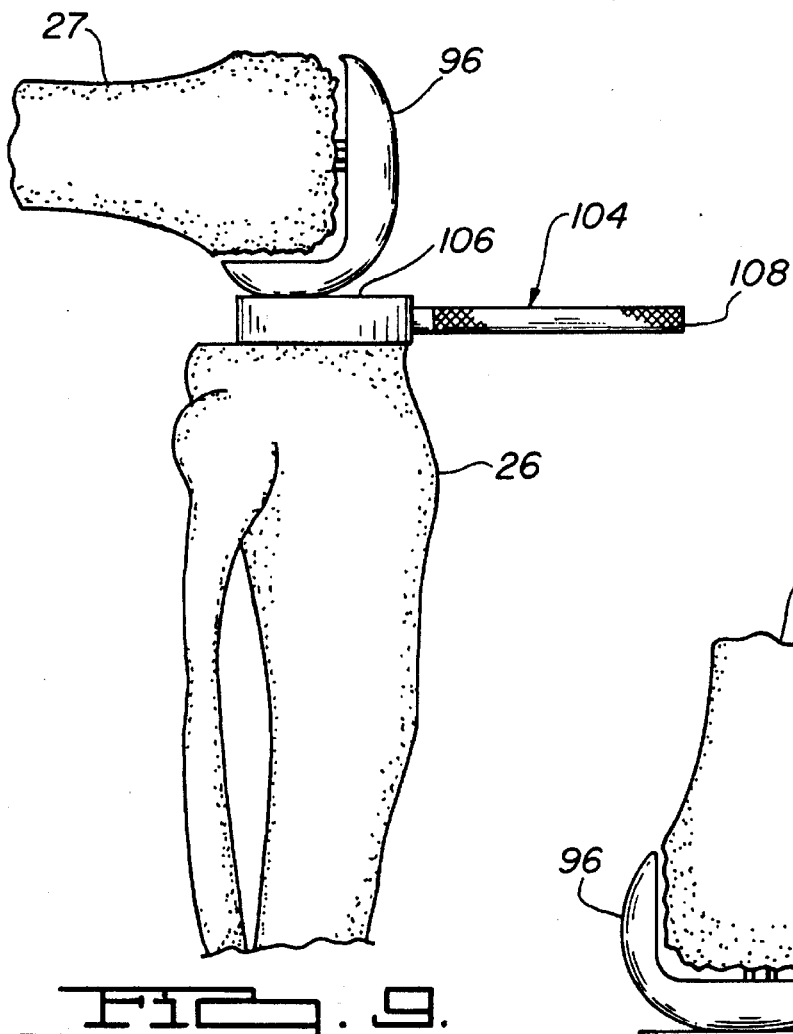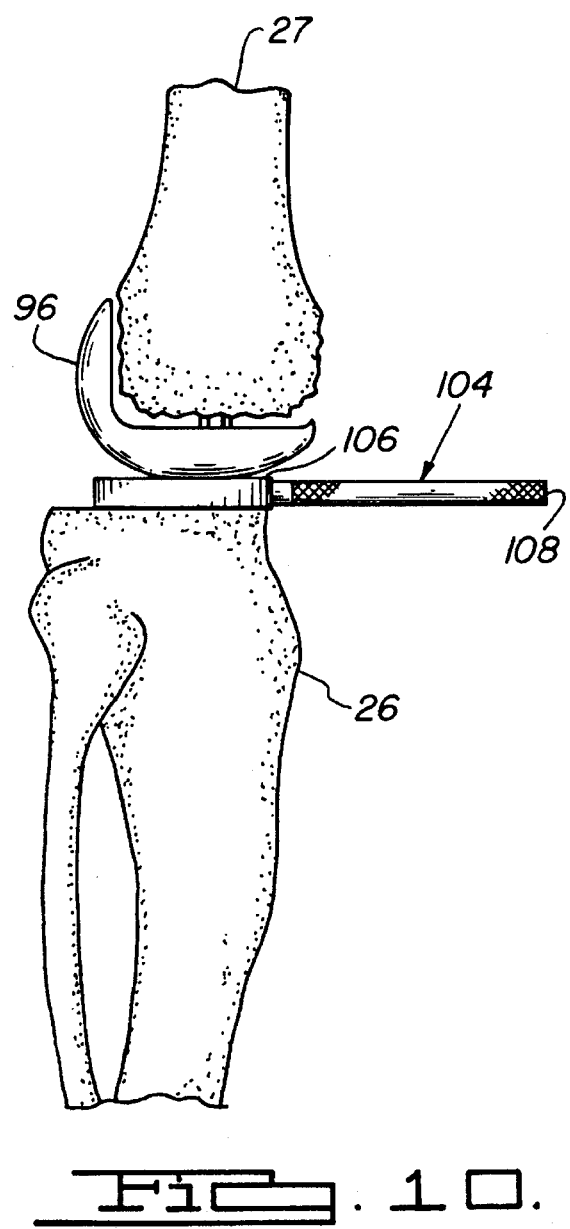
FIG. 9.
FIG. 10.

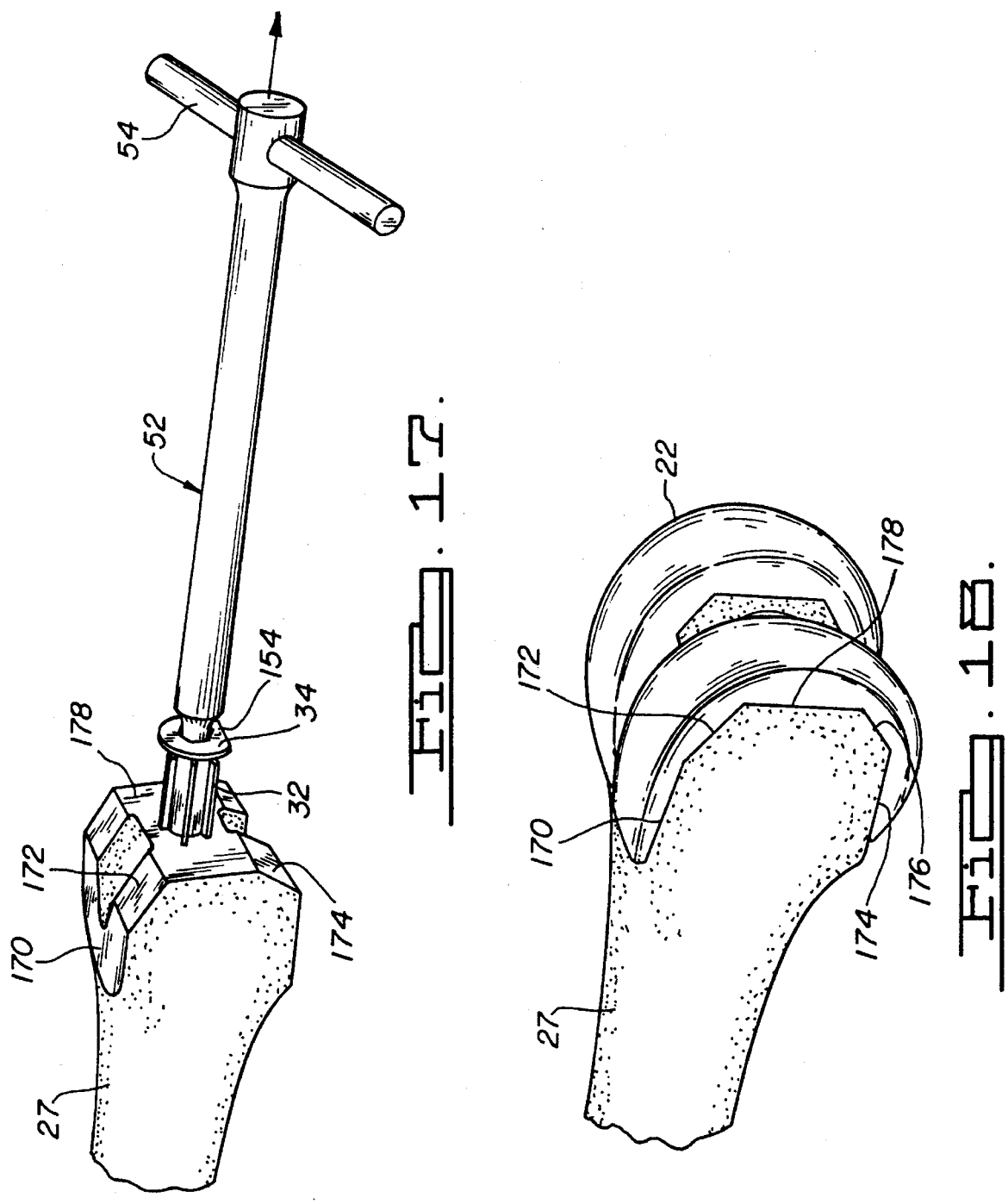

INSTRUMENTATION FOR REVISION SURGERY

BACKGROUND OF THE INVENTION

The present invention relates generally to instrumentation to be used in revision surgery, and more particularly, to instrumentation that allows trial reduction prior to femoral resection.

A natural joint in the human body such as a knee joint may undergo degenerative changes due to a variety of etiologies. When these degenerative changes become advanced and are irreversible, it may ultimately become necessary to replace the natural joint with a prosthetic joint. Such a prosthetic joint often includes several biocompatible components which are formed from high strength synthetic materials. These materials are not only able to accommodate the various loading conditions that the prosthetic joint may encounter, but are also biocompatible with the human body.

While such knee joint prostheses have been effective in replacing the anatomical knee joint, revision surgery is sometimes required to replace a knee joint prosthesis when such factors as bone deterioration occurs. In such revision surgery, the existing femoral component is removed from the distal femur and then the distal femur is prepared to accept the femoral component of a new knee joint prosthesis. In this regard, the tibia is first resected so as to leave a flat surface. The valgus angle of the femur is then determined and a distal resection is made based on the valgus angle. Further femoral resection is performed, the orientation of which is based on the distal resection. Trial reduction is then performed to obtain proper placement of the femoral component.

While revision surgery is generally successful in replacing the primary knee joint prosthesis with a revision knee joint prosthesis, such revision surgery is often relatively complicated. If the femoral component does not fit properly, adjustment cuts, augments or other alternative adjustments must be made. These adjustments are not easily performed and proper positioning of the prosthesis is often difficult to achieve. In addition to the foregoing, revision surgery is often complicated due to bone loss. Specifically, bony landmarks used in primary prosthesis surgery as cutting guides are unavailable due to distal and posterior femoral bone loss.

Accordingly, it is desired to provide a system which allows trial reduction prior to femoral resection, and wherein the trial reduction dictates where resection should be made to accommodate proper placement of the prosthesis.

SUMMARY OF THE INVENTION

Generally, the present invention provides a revision surgery instrumentation system for the femur of a human knee wherein the instrumentation system allows trial reduction prior to femoral resection. The invention also encompasses a method for preparing the distal femur of the human knee for a femoral prosthesis in which trial reduction dictates where resection should be made to accommodate proper placement of the prosthesis.

More specifically, the revision surgery instrumentation of the present invention includes an intramedullary rod, a screw threadably engaged in the rod, a set of angled support members wherein each individual member may be demountably attached to the rod, a set of femoral provisionals, a set of spacer blocks and a set of femoral resection instruments.

An advantage of the present invention is to provide instrumentation for revision surgery in which trial reduction may be performed prior to resection of the femur, and wherein the trial reduction dictates where resection should be made.

Another advantage of the present invention is to provide instrumentation for revision surgery in which the proper size femoral component may be determined with relative ease.

A further advantage of the present invention is to provide instrumentation for revision surgery which does not require use of the boney landmarks available in primary surgery to determine where to place the femoral resection.

Another advantage of the present invention is to provide instrumentation for revision surgery which is more accurately able to accommodate for soft tissue balance with respect to a knee joint prosthesis.

A further advantage of the present invention is to provide instrumentation for revision surgery in which the thickness of the bearing member of the tibial component may be determined with relative ease.

Another advantage of the present invention is to provide instrumentation for revision surgery which is easy to use and accurately determines where femur resection should occur.

BRIEF DESCRIPTION OF THE DRAWINGS

The various advantages of the present invention will become apparent to one skilled in the art by reading the following specification and subjoined claims and by referencing the following drawings in which:

FIG. 5 is a perspective view of an impactor used for driving an intramedullary rod into the intramedullary canal according to the preferred embodiment of the present invention;

FIG. 6 is a perspective view of a screw and a hex driver for threading the screw into the intramedullary rod according to the preferred embodiment of the present invention;

FIG. 9 is a side elevational view of a femur and tibia at 90° of flexion shown with the femoral provisional and spacer block in place according to the preferred embodiment of the present invention;

FIG. 10 is a side elevational view of a femur and tibia in full extension shown with the femoral provisional and spacer block in place according to the preferred embodiment of the present invention;

FIG. 17 is a perspective view of an extractor removing an intramedullary rod from the femur according to the preferred embodiment of the present invention;

FIG. 18 is a perspective view of an appropriately shaped distal femoral surface showing the femoral component of a knee joint prosthesis affixed thereto according to the preferred embodiment of the present invention;

DETAILED DESCRIPTION OF THE PREFERRED EMBODIMENTS

It should be understood that while this invention is described in connection with a particular example thereof, the scope of the invention need not be so limited. Rather, those skilled in the art will appreciate that the following teachings can be used in a much wider variety of applications than the examples specifically mentioned herein.

Figure 1:
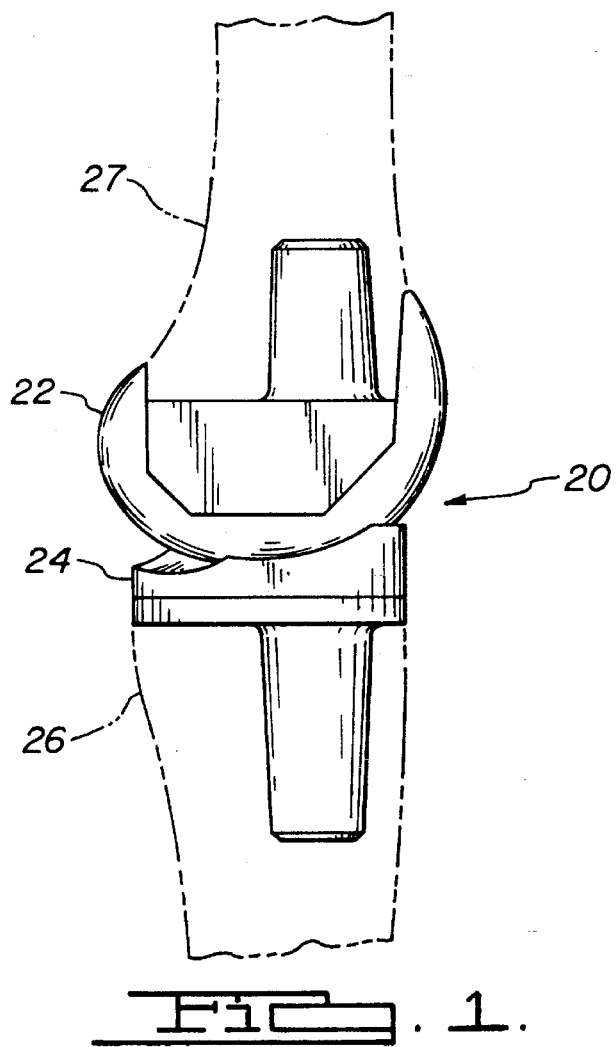
FIG. 1 is a sagittal elevational view of a left knee joint having a knee joint prosthesis, with the tibia and the femur of the natural knee shown in phantom.

Referring now to FIG. 1, there is shown a knee joint prosthesis 20 having a femoral component 22 and a tibial component 24. The femoral component 22 and the tibial component 24 are shown as being functionally depicted as being secured to a tibia 26 and femur 27 of a surgically resected right knee joint, with the tibia 26 and femur 27 being shown in phantom. It will be understood that any suitable knee joint prosthesis may be utilized in the present invention. It will be similarly understood that while a left knee joint prosthesis 20 is shown, the present invention may be used for both right and left knee joint prosthesis surgery.

Figure 2:
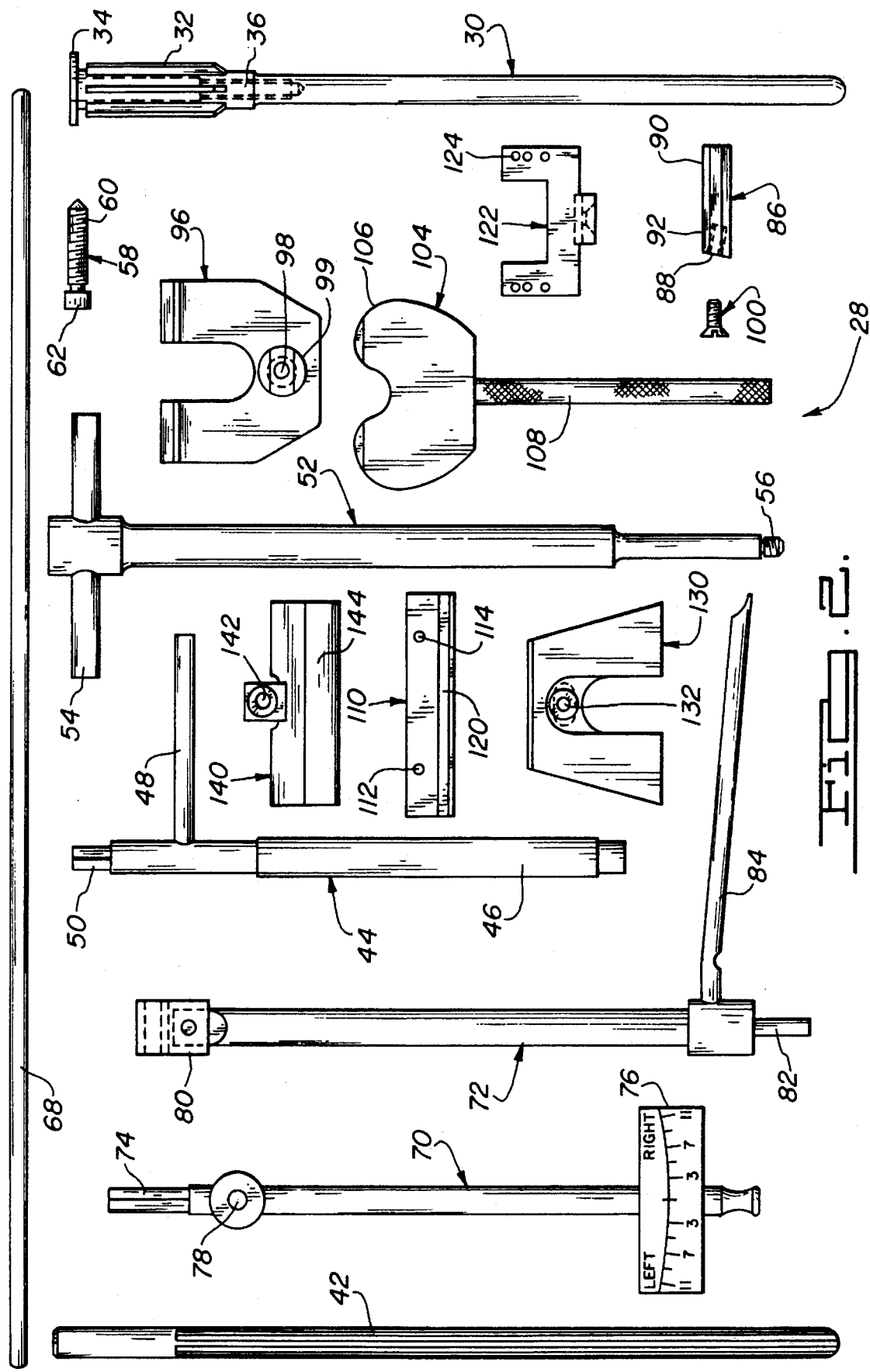
FIG. 2 is a plan view of the set of surgical instruments for revision surgery according to the preferred embodiment of the present invention.

Referring now to FIG. 2, there is shown the set of surgical instruments, generally designated by the numeral 28, according to the preferred embodiment of the present invention. The set of surgical instruments is used to provide means for adjustably positioning a plurality of resection guides in response to the provisional placement of the femoral component 22 of the knee joint prosthesis 20. The set of surgical instruments 28 comprises an intramedullary rod 30 which is used for positioning the various femoral shaping instrumentation discussed below. The intramedullary rod 30 is straight and comprises a plurality of flutes 32 which are used to prevent rotation of the intramedullary rod 30 when the intramedullary rod 30 is located in the femur 27. In addition, the intramedullary rod 30 also includes a flange portion 34 which is used when impacting the intramedullary rod 30 into the femur 27. The intramedullary rod 30 also comprises a blind bore 36 as well as a hex portion 38. The blind bore 36 includes a threaded end portion 40 located at one end thereof which is used to threadably engage a screw described in more detail below. The hex portion 38 is used for attaching other instrumentation to intramedullary rod 30.

The length of the intramedullary rod 30 is approximately the length of the stem of the prosthesis that will be later utilized during the revision surgery. The diameter of the intramedullary rod 30 is approximately 9 mm. However, the diameter of the intramedullary rod 30 may be somewhat larger if desired.

To provide means for forming a cavity in the intramedullary canal of femur 27, the set of surgical instruments 28 further includes a reamer 42. The reamer 42 is used to form a cavity in the intramedullary canal so that intramedullary rod 30 may be inserted into the intramedullary canal. While the reamer 42 may be rotated by a drill, the reamer 42 may also have a T-shaped handle which allows manual rotation of the reamer. As will be more fully described below, the reamer 42 is initially inserted into a hole formed by a drill and is then rotated to form the cavity.

To provide means for inserting the intramedullary rod 30 in the intramedullary canal, an impactor 44 is provided. The impactor 44 is used for driving the intramedullary rod 30 into the intramedullary canal and comprises an elongated member 46 and a vertical alignment rod 48 attached thereto at a right angle. The vertical alignment rod 48 is used to align intramedullary rod 30 in the intramedullary canal as will be described below. In addition, the impactor 44 comprises a hex portion 50 which corresponds to the hex portion 38 of intramedullary rod 30. The hex portion 50 allows the impactor 44 to engage the intramedullary rod 30 in a relatively secure fashion when the impactor 44 is driving the intramedullary rod 30 into the intramedullary canal.

The set of surgical instruments 28 further includes an extractor 52. The extractor 52 is used for extracting intramedullary rod 30 from the intramedullary canal after the femur 27 has been resected as described below. The extractor 52 includes a handle portion 54 which is used for grasping and rotating the extractor 52. In addition, the extractor 52 also comprises a threaded end portion 56 which is operable to engage the threaded portion 40 of the intramedullary rod 30.

To provide means for adjusting the position of a provisional femoral component described below, the set of surgical instruments 28 further includes a threaded member in the form of a screw 58. The screw 58 is used for adjusting the effective depth of the blind bore 36 of intramedullary rod 30 so as to establish a locating surface for the support member described below. The screw 58 comprises a threaded portion 60 which is able to engage the threaded portion 40 of the intramedullary rod 30. In addition, the screw 58 includes a head portion 62 having a hex-shaped bore portion 64. The hex-shaped bore portion 64 of the head portion 62 is used to allow the screw 58 to be inserted and extracted with a hex driver described below.

Figure 7:
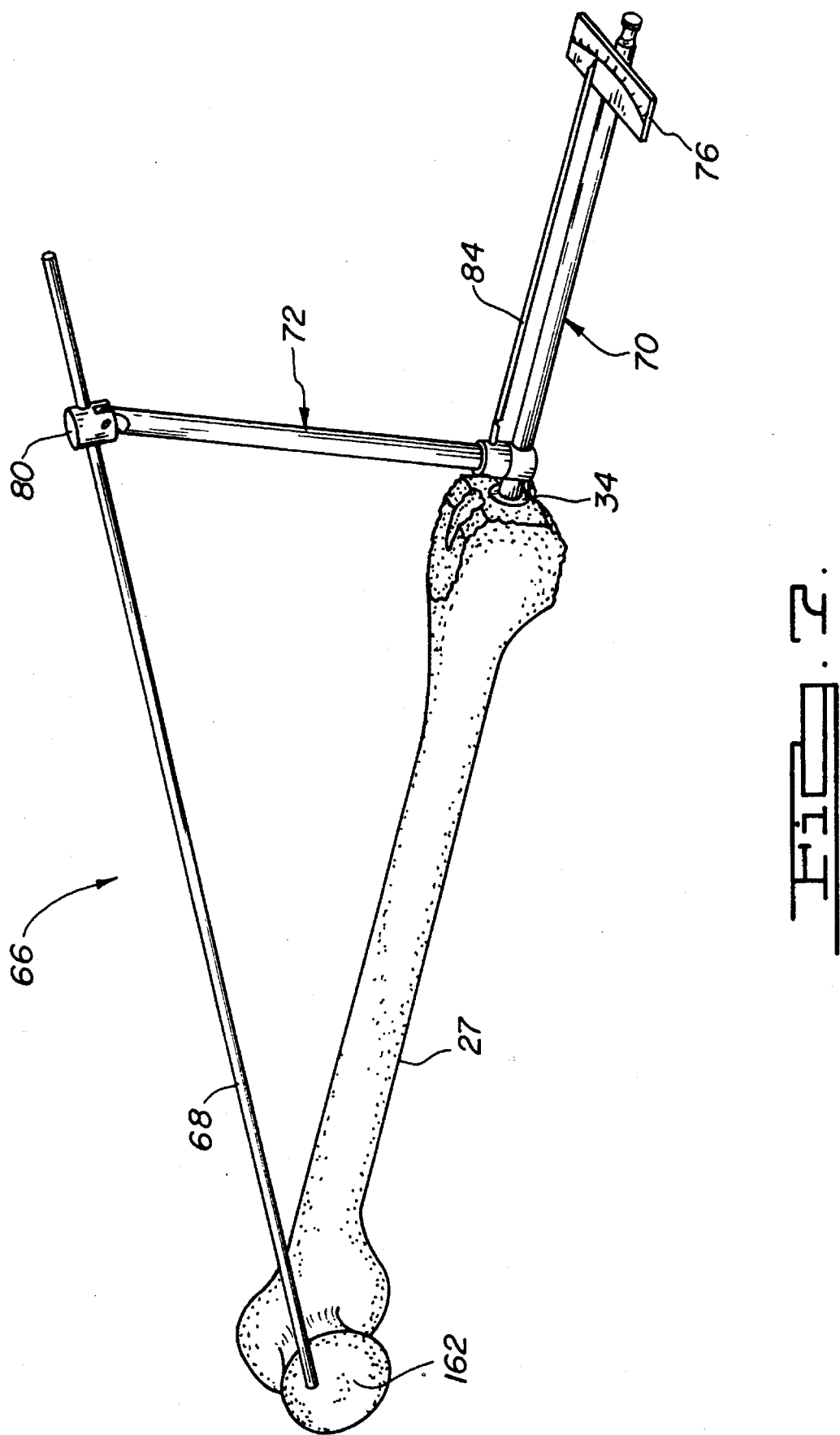
FIG. 7 is a perspective view of an angle guide used for measuring the valgus angle of the femur according to the preferred embodiment of the present invention.

To provide means for measuring the valgus angle of the femur 27, the set of surgical instruments 28 further includes an angle guide 66 which is best shown in FIG. 7. The angle guide 66 is used to determine the valgus angle of the femur 27 and includes a rod 68, an extension member 70 and a direction member 72. The extension member 70 comprises a hex portion 74 which is operable to engage the hex portion 38 of the intramedullary rod 30. In addition, the extension member 70 comprises an angle measuring device 76 which is used for measuring the angle indicated by a pointer member which is located on the direction member 72 as described below. The extension member 70 also comprises a bore 78 which is used for attaching the direction member 72 to the extension member 70.

The direction member 72 of the angle guide 66 comprises a rotating head 80 having an aperture (not shown) which is used for receiving the rod 68. In addition, the direction member 72 includes an insertion member 82 which is operable to be received by the bore 78 of the extension member 70. In addition, the directional member 72 includes a pointer member 84 which is used to indicate the valgus angle of the femur 27 on the angle measuring device 76 as described below.

To provide means for attaching certain instruments to the intramedullary rod 30 at the valgus angle of the femur 27, an angled support member 86 is also provided. The exterior of the angled support member 86 is hexed shaped so as to be operable to be inserted into the hex portion 38 of intramedullary rod 30. The angled support member 86 includes an angled end portion 88 and a flat end portion 90. The angled end portion 88 is angularly displaced from a plane perpendicular to the axial centerline of the angled support member 86 by the valgus angle determined by the angle guide 66. Because the valgus angles for different femurs will vary, the set of surgical instruments 28 includes a plurality of angled support members each having a different valgus angle. In addition, the angled support member 86 comprises a threaded bore 92 (shown in phantom in FIG. 2) at angled end 88 which is used to attach angled support member 86 to other instruments. The set of angled support members 86 have angles varying from about 5° to about 12°. Preferably, the valgus angle associated with each of the angled support members 86 is located at the flat end portion 90 of the angled member.

To provide second means for attaching angle support member 86 to other instrumentation, angle support member 86 includes threads 94 at angled end 88 of angled support member 86. The threads 94 on angle support member 86 may then be threadably engaged with threaded portions of other instrumentation as described below.

To provide means for performing trial reduction prior to resection, the set of surgical instruments 28 further includes a femoral provisional 96. The femoral provisional 96 is used for determining the proper size of the femoral component 22 as well as the proper alignment of resection instrumentation described below. The femoral provisional 96 comprises a passage 98 which is used for attaching the femoral provisional 96 to angled support member 86 by means of the attachment screw described below. The external contour of the femoral provisional 96 is similar to the external surface of the femoral component but thinner so as to provide clearance on bone that may be lost. Finally, the femoral provisional 96 also includes a flange portion 99 used to prevent rotation of the angled support member 86 in a manner described below. In the preferred embodiment of the present invention, the set of surgical instruments 28 includes several femoral provisionals 96 which are of different sizes. Each of the femoral provisionals 96 has about a 5 mm difference in width and about a 4 mm difference in depth. The set of femoral provisionals ranges in size from about 55 to about 80.

To provide means for attaching angled support member 86 to the femoral provisionals 96, a threaded member such as the attachment screw 100 is provided. The attachment screw 100 is used to attach the angled hex piece 86 to the femoral provisionals 96 as well as to other instrumentation described below. The attachment screw 100 includes a threaded portion which is able to engage the threaded bore 92 of the angled support member 86. Accordingly, by inserting the attachment screw 100 through the hole in the femoral provisional and allowing the threads of the attachment screw 100 to engage the threaded bore 92 of the angled support member 86, the femoral provisional may be secured to the angled support member 86.

The set of surgical instruments 28 further includes a spacer block 104. The spacer block 104 is used for determining the thickness of the tibial component 24 of a knee prosthesis 20 as well as the proper positioning of the various resection guides as more fully described below. The spacer block 104 comprises a spacer pad 106 which is used for measuring the distance between the tibia 26 and the femoral provisional 96. In addition, the spacer block 104 comprises a handle 108 which is used to move the spacer block 104 from one position to another.

To provide means for guiding a cutting blade during distal resection, a distal resection guide 110 is provided. The distal resection guide 110 comprises a plurality of holes 112 and 114 which are used for attaching the distal resection guide 110 to the femur 27. The pins 116 and 118 are placed in holes 112 and 114 and are used to hold the distal resection guide 110 in the proper position on the femur 27. In addition, the distal resection guide 110 also comprises a cutting guide surface 120 which is used to align the cutting blade in the proper position for distal resection.

The set of surgical instruments 28 further comprises a distal drill guide 122. The distal drill guide 122 is used for positioning drilled holes in the femur 27 which are used to align the distal resection guide 110. The distal drill guide 122 comprises a plurality of holes 124 which accept drill bits which are connected to a drill. The distal drill guide 122 also comprises a stem 126 having an aperture 128. The aperture 128 is used for attaching the distal drill guide 122 to the angled support member 86.

To provide means for guiding a cutting blade during anterior and posterior resection, the set of surgical instruments 28 further comprises an anterior-posterior resection guide 130. The anterior-posterior resection guide 130 includes an aperture 132 which is used for attaching the anterior-posterior resection guide 130 to the angled support member 86. In addition, the anterior-posterior resection guide 130 comprises a cutting guide surface 134 and cutting guide surfaces 136 and 138 which are used to align a cutting blade in the proper position for anterior-posterior resection as will be more fully described below. The anterior-posterior resection guide 130 may also have slots or other types of surfaces which may be used to facilitate resection.

The set of surgical instruments 28 further includes a chamfer resection guide 140. The chamfer resection guide 140 is used to guide a cutting blade in making a chamfer resection. The chamfer resection guide 140 comprises an aperture 142 which is used to attach the chamfer resection guide 140 to the angled support member 86. In addition, the chamfer resection guide 140 comprises a cutting guide surface 144 and a cutting guide surface 146 which are used to align cutting blade 148 in the proper position for chamfer resection.

The set of surgical instruments 28 described above is used to prepare the femur 27 to accept a femoral component of a knee joint prosthesis during revision surgery. The following is a detailed description of the method for using the set of surgical instruments 28 of the present invention. It will be appreciated, however, that the following discussion concerns only one method for using the set of surgical instruments 28. Other methods will be appreciated by those skilled in the art.

Figure 3:
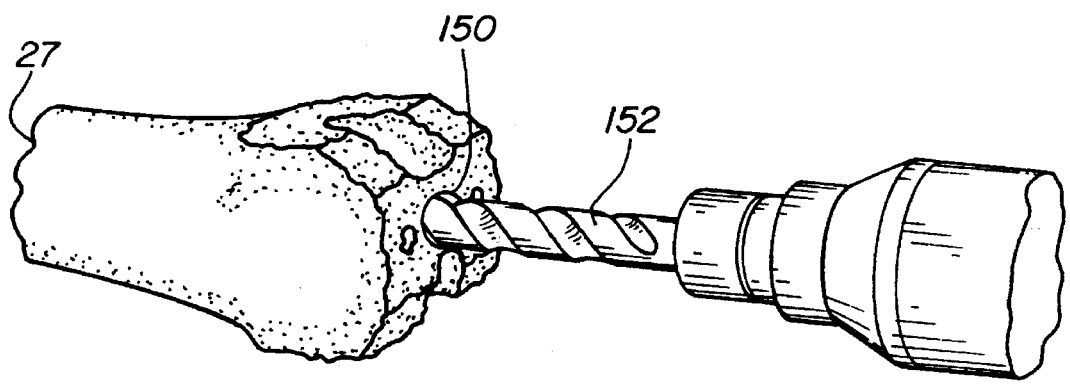
FIG. 3 is a perspective view of a drill forming a hole in the distal surface of a femur according to the preferred embodiment of the present invention.

Referring now to FIG. 3, the femur 27 is shown after the primary implant (not shown) has been removed. After the primary implant has been removed, a hole 150 is drilled in the distal surface of the intercondylar notch of femur 27. Standard instrumentation such as drill 152 depicted in FIG. 3 may be used.

Figure 4:
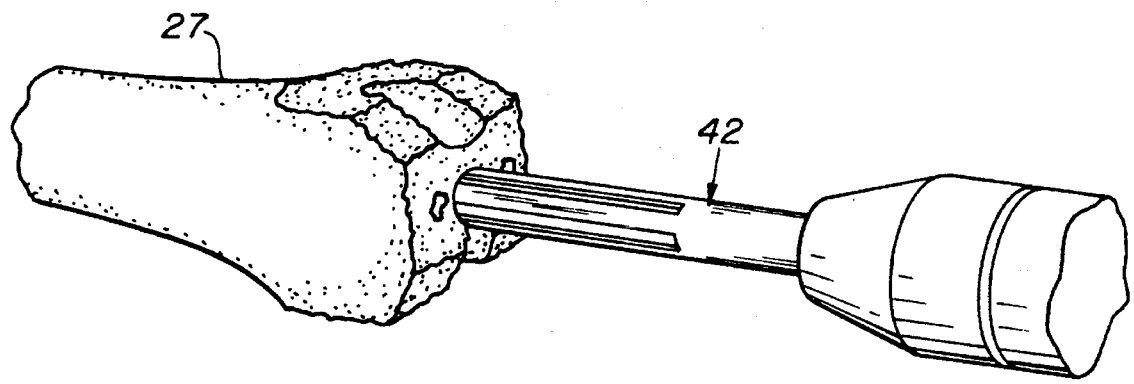
FIG. 4 is a perspective view of an intramedullary reamer entering the intramedullary canal according to the preferred embodiment of the present invention.
Figure 8:
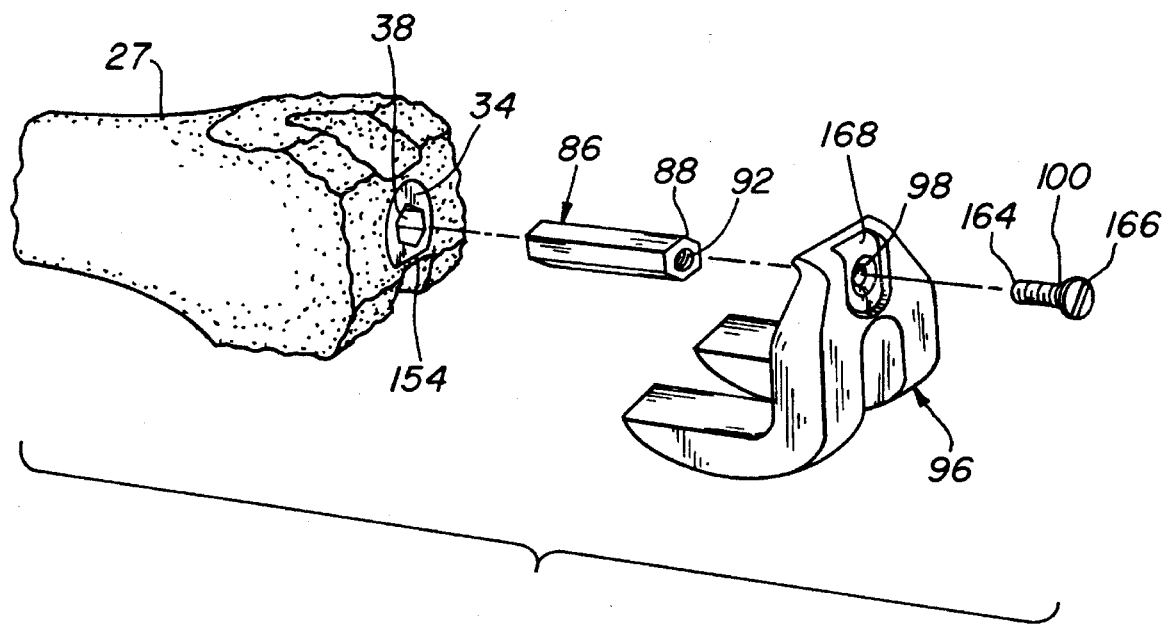
FIG. 8 is a perspective view showing the use of the femoral provisional according to the preferred embodiment of the present invention.

A reamer 42 is then inserted into the hole 150 created by the drill 152 as shown in FIG. 4. The reamer 42 is then rotated so as to form a cavity within the intramedullary canal. Preferably, the cavity extends approximately 6 to 8 inches into the intramedullary canal. Once the reamer 42 is removed from the intramedullary canal, the hex portion 50 of the impactor 44 is inserted into the corresponding hex portion 38 of the intramedullary rod 30. The orientation of the intramedullary rod 30 in relation to the impactor 44 is such that the flat portion 154 of the intramedullary rod 30 is posterior to allow for clearance of the posterior cruciate ligament (when the ligament is retained) as shown in FIG. 5. In addition, the vertical alignment rod 48 should be vertical to the femur 27 to assure proper alignment of the intramedullary rod 30. Alternative methods of alignment include using a horizontally oriented alignment rod and employing the epicondyles as landmarks.

The intramedullary rod 30 is then placed into the cavity 156 and driven into the cavity 156 formed by the reamer 42 as shown in FIG. 5. In this regard, a mallet 158 may be employed to assist the insertion of intramedullary rod 30. The intramedullary rod 30 is inserted into the canal until the flutes 32 of intramedullary rod 30 engage the femur 27. In addition, the flange portion 34 of the intramedullary rod 30 should be level with the remaining bone to assure proper positioning. Further manipulations such as additional rods or sleeves may be utilized to assure that the intramedullary rod 30 fits securely in the cavity formed in the intramedullary canal. If the intramedullary rod 30 requires readjustment, extractor 52 may be employed to remove and reinsert the intramedullary rod 30.

Figure 11:
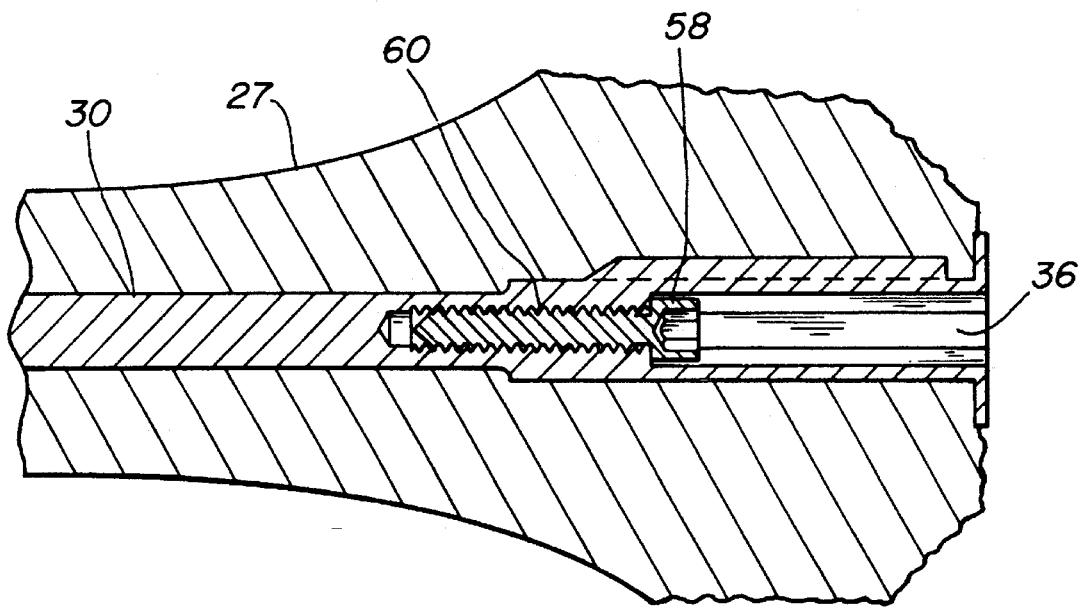
FIG. 11 is a cross-sectional view of a femur showing a screw in the bore of an intramedullary rod in its most proximal position according to the preferred embodiment of the present invention.
Figure 12:
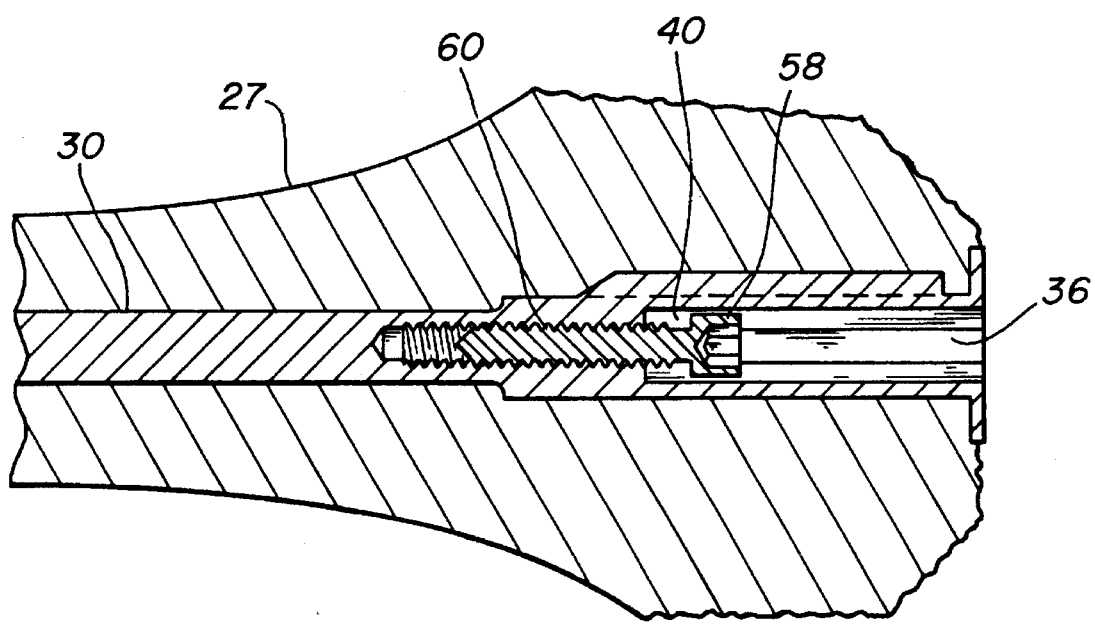
FIG. 12 is a cross-sectional view of a femur showing a screw in the bore of an intramedullary rod in a position more distal than that shown in FIG. 11, according to the preferred embodiment of the present invention.

Once the intramedullary rod 30 is properly inserted, the screw 58 is inserted into the blind bore 36 of the intramedullary rod 30 with the hex driver 160 as shown in FIG. 6. As this occurs, the threaded portion 60 of the screw 58 engages the threaded portion 40 of the blind bore 36. By rotating the hex driver 160 when it is engaged with the hex portion 64 of the screw 58, the screw 58 may be moved distally and proximally within the blind bore 36. The position of the screw 58 within the blind bore 36 determines the depth of the blind bore 36. In this regard, FIG. 11 shows the screw 58 positioned as far proximally as possible, while FIG. 12 shows the screw 58 positioned distally with respect to the position shown in FIG. 11. In the method of the present invention, the screw 58 should be first positioned proximally as shown in FIG. 11 to allow for maximum adjustability.

Once the screw 58 is inserted into the blind bore 36, the valgus angle of the femur is determined by using the angle guide 66. In this regard, the extension member 70 is attached to the intramedullary rod 30 by inserting the hex portion 74 of the angle guide 66 into the hex portion 38 of the intramedullary rod 30. The insertion member 82 of the direction member 72 is then inserted into the bore 78 of the extension member 70 so that the direction member 72 is vertical to the femur 27 and the pointer 84 is directly above the angle measuring device 76. The rod 68 is then inserted into an aperture of the rotating head 80 of the direction member 72. As shown in FIG. 7, the free end of the rod 68 is placed to the center of the femoral head 162 located at the proximal end of the femur 27. The center of the femoral head 162 may be determined by various methods. Once the rod 68 is placed on the center of the femoral head 162, the pointer 84 will be directed to a number on the angle measuring device 76. This number represents the valgus angle of the femur 27. It will be appreciated that other methods for determining the valgus angle may be employed, such as x-ray evaluation. Once the valgus angle is determined, the angle guide 66 is disassembled and the extension member 70 is removed from intramedullary rod 30.

The angled support member 86 is then selected which has an angled end portion 88 which is angularly displaced by an angle which is closest to the previously determined valgus angle. A femoral provisional 96 of the appropriate size is also selected. A variety of methods for selecting the size of the femoral provisional 96 may be utilized such as comparing the femoral provisional 96 to the remaining bone, examining the knee not engaged in surgery and analyzing x-rays taken prior to primary replacement surgery.

Once a femoral provisional 96 of the appropriate size is chosen, the screw 100 is inserted through the passage 98 of the femoral provisional 96 until the end portion 164 of the screw 100 passes through the passage 98 and the head 166 of screw 100 is resting on the femoral provisional 96. The threaded blind bore 92 of the selected angled support member 86 is threadably engaged with the screw 100 so that the angled support member 86 is securely fastened to the femoral provisional 96. Because two sides of the angled support member 86 engage the flange portion 99 (see FIG. 2), the flange portion 99 prevents rotation of the angled support member 86. The angled support member 86 is connected to the femoral provisional 96 in one of two orientations in order for it to properly function depending on whether a right or left knee is involved. That is, by rotating the angled support member 86 by 180°, the angled support member 86 may accommodate either a left knee or a right knee.

The knee is then placed in 90° of flexion and the spacer blocks 104 of different thicknesses are inserted between the femoral provisional 96 and the flat surface of the tibia 26. This is shown in FIG. 9. The surgeon then determines which spacer block 104 provides a tight fit against the forces of the soft tissues. As shown in FIG. 10, the same procedure is used when the knee is in full extension. Again, a determination is made as to which spacer block 104 provides a tight fit against the soft tissues. If the same thickness spacer block 104 provides the best fit in both flexion and extension, the correct placement of the femoral component of the prosthesis is that of the femoral provisional 96 and the correct thickness of the tibial component is that of the spacer block 104. If the thickness of the spacer block 104 in flexion and extension is not the same, further manipulations as described below must be made so that the same thickness of the spacer block 104 is used in both flexion and extension.

If the thickness of the spacer block 104 is smaller in flexion than in extension, the femoral provisional 96 is moved distally. Accordingly, the angled support member 86 and the femoral provisional 96 are removed from the intramedullary rod 30. The screw 58 within the blind bore 36 is adjusted with the hex driver 160 so that it is more distally located. Optimally, the screw 58 is moved the same distance as the difference in the thickness between the spacer block 104 in flexion and the spacer block 104 in extension. For example, if in flexion the thickness of the spacer block 104 is 12 mm and in extension, the thickness of the spacer block 104 is 20 mm, the screw 58 should be moved distally 8 mm so the femoral provisional 96 is also moved distally 8 mm. The distance which the screw 58 is moved may be calculated by determining the distance between the threads on the threaded portion 60 and the number of turns made with the hex driver 160. Alternative means for determining the distance the screw 58 is moved may also be employed such as inserting a measuring device into the blind bore 36 until it rests on the head 62 of the screw 58 before the screw 58 has been moved, and then again after the screw 58 has been moved.

The angled support member 86 with the femoral provisional 96 attached is again inserted into the blind bore 36 of the intramedullary rod 30 until the angled support member 86 contacts the head 62 of the screw 58. The spacer blocks 104 of various thicknesses are again inserted between the femoral provisional 96 and the flat surface of the tibia 26 to determine which thickness of spacer block 104 provides a tight fit against the forces of the soft tissue during both flexion and extension. If the thickness of the spacer block 104 is the same in both flexion and extension, the femoral provisional 96 is of the appropriate size and is in the proper position. In addition, the thickness of the bearing member of the tibial component 24 will be the same thickness as the spacer block 104.

If the thickness of the spacer block 104 is greater in flexion than the thickness of the spacer block 104 in extension, a larger femoral provisional 96 is used. The larger femoral provisional 96 is attached to the angled support member 86 and the intramedullary rod 30 as previously described. The thickness of the spacer block 104 in flexion and extension is again determined. If the thickness of the spacer block 104 is not the same in flexion and extension, the femoral provisional 96 is replaced with a different size femoral provisional 96 or the screw 58 may be moved distally or proximally within bore 36. If these manipulations do not provide for the spacer block 104 having the same thickness in both flexion and extension, the intramedullary rod 30 may be impacted further into the femur 27.

Once the thickness of the bearing of the tibial component 24 and the size and placement of the femoral provisional 96 are determined, the angled support member 86 is removed from the femoral provisional 96 while the screw 58 is left in the same position in the blind bore 36. This position will be used to properly align the various femoral shaping instruments on the distal femoral surface prior to resection as described below.

Figure 13:
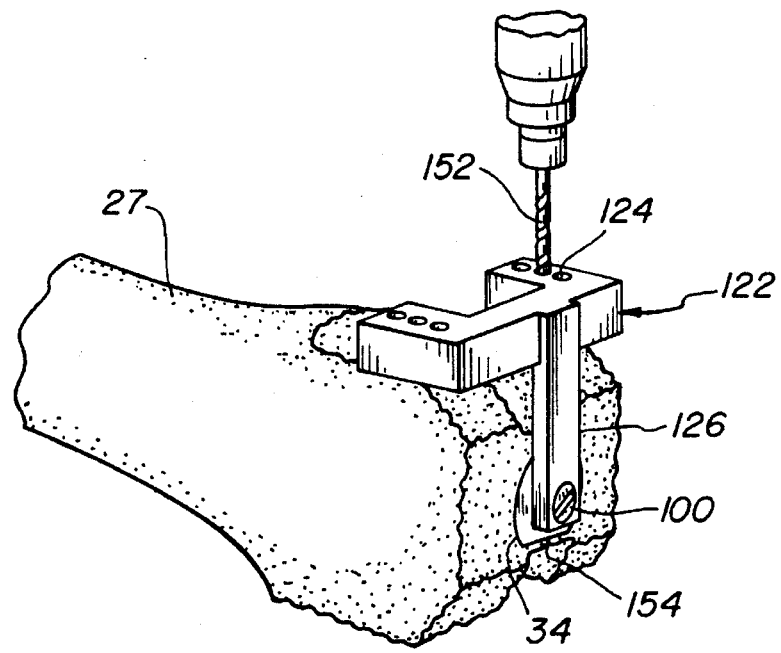
FIG. 13 is a perspective view of a distal drill guide according to the preferred embodiment of the present invention.

The angled end portion 88 of the angled support member 86 is attached to the distal drill guide 122 and the flat end 90 of angled support member 86 is inserted into the blind bore 36 of the intramedullary rod 30 until the angled support member 86 bottoms out against the head 62 of the screw 58 as shown in FIG. 13. Two holes are then drilled in the femur 27 based on the holes 124 of the distal drill guide 122. The angled support member 86 and the distal drill guide 122 are then removed and the angled support member 86 is then removed from the distal drill guide 122.

Figure 14:
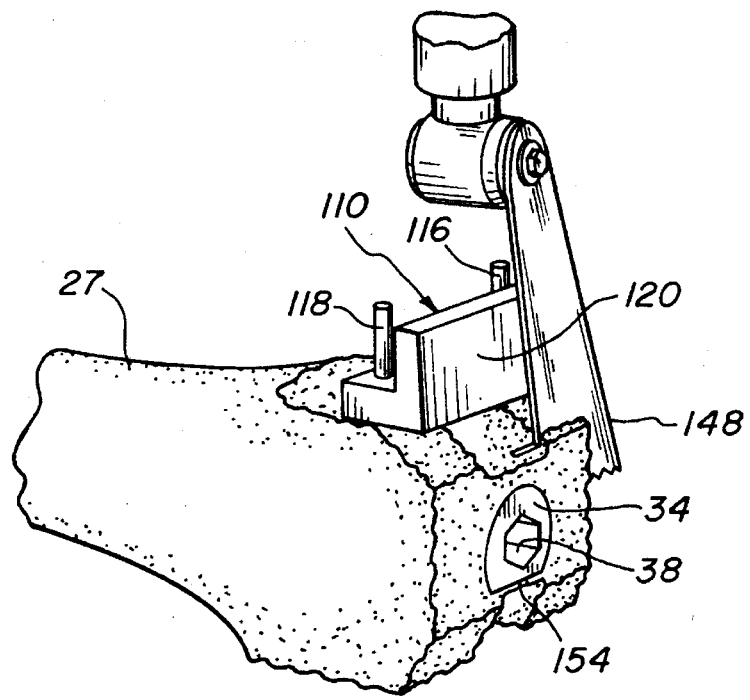
FIG. 14 is a perspective view of a distal resection guide according to the preferred embodiment of the present invention.

As shown in FIG. 14, the distal resection guide 110 is attached to the femur 27 by placing the pin 116 and the pin 118 in the holes 112 and 114 of the distal resection guide 110 and in the holes in the femur 27 formed by the distal drill guide 122. A distal resection is then made by a cutting blade 148 based on the placement of the distal resection guide 110. The distal resection guide 110 is then removed from the femur 27.

The angled end portion 88 of the angled support member 86 is then placed in the aperture 132 of anterior-posterior femoral resection guide 130 and the screw 100 is threadably engaged in the blind bore 92 of the angled support member 86 to attach the angled support member 86 to the anterior-posterior resection guide 130. The flat end 90 of the angled support member 86 is then inserted into the hex portion 38 of the intramedullary rod 30 until it contacts the head 62 of the screw 58.

Figure 15:
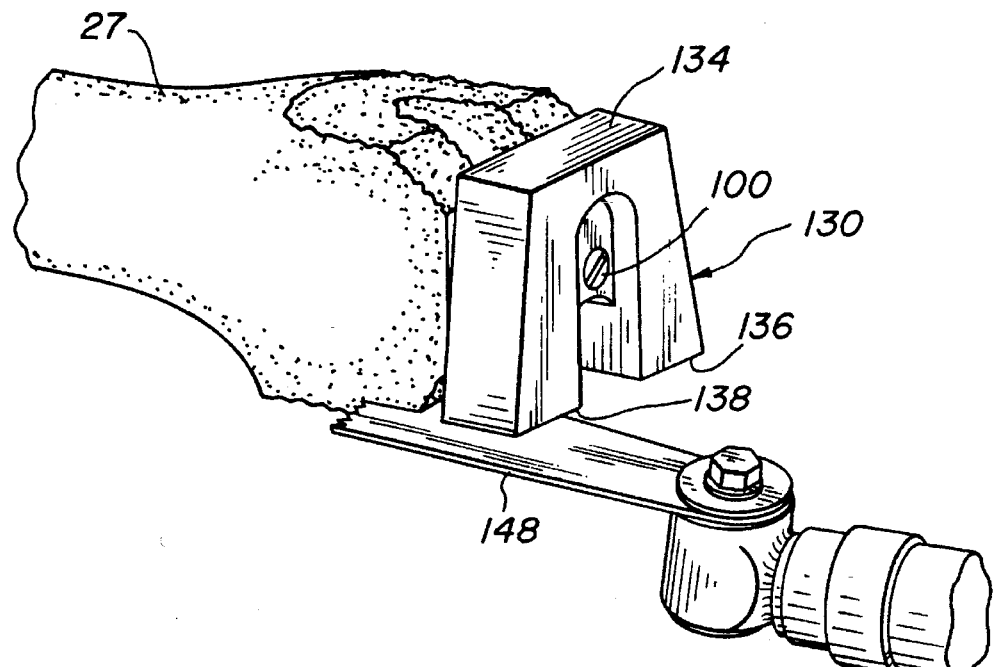
FIG. 15 is a perspective view of an anterior-posterior resection guide according to the preferred embodiment of the present invention.

As shown in FIG. 15, anterior and posterior resections are then made by a cutting blade 148 which uses the anterior-posterior resection guide 130 to guide the cutting blade 148. After the anterior and posterior resection have been performed, the angled support member 86 and the anterior-posterior resection guide 130 are removed. The angled support member 86 is removed from the anterior-posterior resection guide 130.

Figure 16:
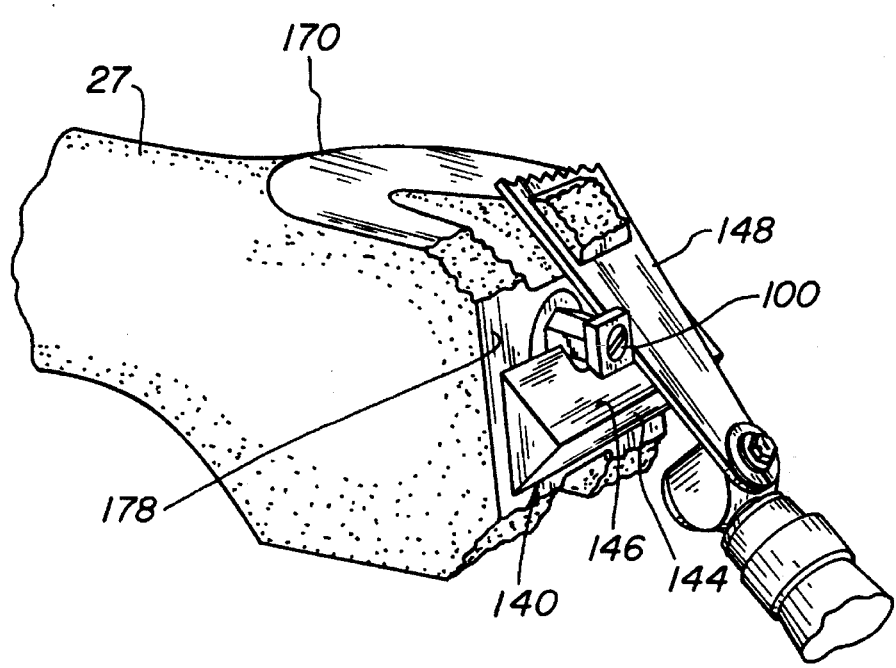
FIG. 16 is a perspective view of a chamfer resection guide according to the preferred embodiment of the present invention.

The angled end portion 88 of the angled support member 86 is then placed in the aperture 142 of the chamfer resection guide 140 and the screw 100 is threadably engaged in the blind bore 92 of the angled support member 86 to attach the angled support member 86 to the chamfer resection guide 140. The flat end 90 of the angled support member 86 is then inserted into the hex 38 of the intramedullary rod 30 until it contacts on the head 62 of the screw 58. As shown in FIG. 16, the chamfer resections are then made by a cutting blade 148 using the chamfer resection guide 140 to guide the cutting blade 148. The angled support member 86 attached to the chamfer resection guide 140 is then removed from the intramedullary rod 30 and the angled support member 86 is removed from the chamfer resection guide 140.

The intramedullary rod 30 is then removed from the intramedullary canal using the extractor 52 as shown in FIG. 17. In this regard, the screw 58 is first removed from the intramedullary rod 30. The extractor 52 is then inserted into the blind bone 36 of the intramedullary rod 30 so that the threaded portion 56 of the extractor 52 engages the threaded portion 40 of the intramedullary rod 30. Force is exerted in the direction of the arrow in FIG. 17 by grasping and pulling on the handle 54 of the extractor 52.

As will be appreciated by those skilled in the art, the surfaces of the femur 27 which receive the femoral components of a knee joint prosthesis 20 have been resected. FIG. 18 shows the resulting shaped distal femoral surface of the femur 27 with resected anterior surfaces 170 and 172 and resected posterior surfaces 174 and 176, situated about the distal femoral surface 178. The shaped distal femoral surface is fitted with a femoral component 22 of a knee joint prosthesis 20 of the type well-known in the art having an interior surface selected to properly fit over the shaped distal femoral surface. It will be appreciated that other bone may have to be removed prior to fixing a femoral component 22 of a knee prosthesis 20.

Figure 19:
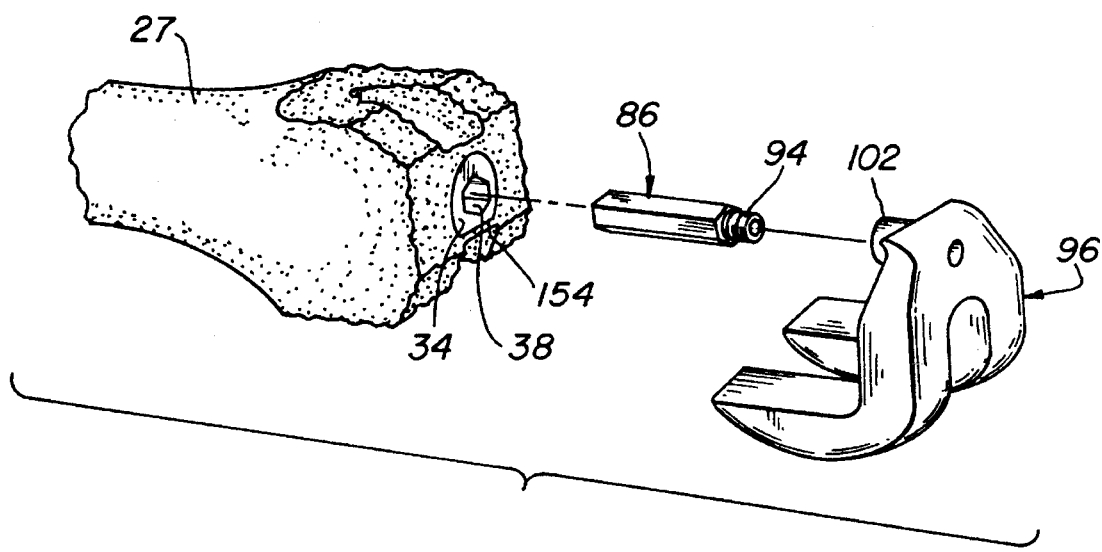
FIG. 19 is a perspective view of a threaded angled support member and a femoral provisional having a threaded cylindrical member according to another embodiment of the present invention.

In an alternative embodiment, as shown in FIG. 19, the threads 94 of the angled support member 86 may be threadably engaged with the threaded cylindrical member 102 of the femoral provisional 96 so that angled support member 86 is securely fastened to the femoral provisional 96. The flat end 90 of the angled support member 86 is then inserted into the intramedullary rod 30 until the femoral provisional 96 bottoms out against the head 62 of screw 58. By utilizing this method, the femoral provisional 96 is positioned on the distal end of the femur 27 based on the previously determined valgus angle of femur 27.

Figure 20:
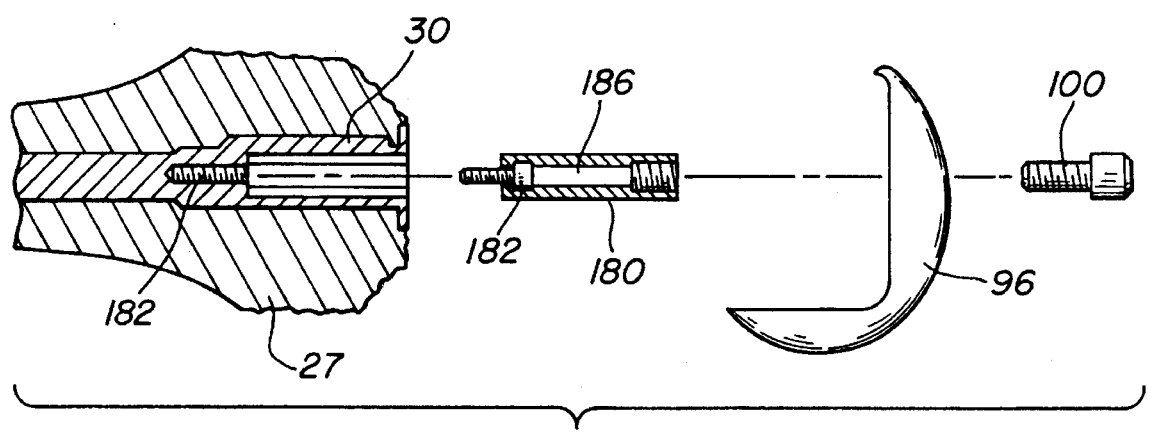
FIG. 20 is a perspective view of a threaded angled support member and a femoral provisional according to yet a further embodiment of the present invention.

In yet a further alternative embodiment of the present invention which is shown in FIG. 20, the set of surgical instruments 28 includes an angled support member 180 having an internal threaded member in the form of a screw 182. The screw 182 is able to threadably engage a threaded portion 184 of the blind bore 36 so as to secure the angled support member 180 to the blind bore 36. Because the support member 180 includes a central bore 186, the screw 182 may be rotated while the support member 180 is attached to the intramedullary rod 30 to adjust the positions of the femoral provisional 96. The angled support member 180 may be also secured to the anterior/posterior resection guide 132, the chamfer resection guide 140 as well as the drill guide 122 during resection in a manner similar to that described below.

It will be appreciated that the foregoing description of the preferred embodiment of the invention is presented by way of illustration only and not by way of any limitation. For example, the impactor and the extractor may be combined so that both insertion and extraction are performed with the same instrument. In addition, a calibrated distractor may be used to balance the soft tissues especially in extension. For example, the support member may have different cross-sections other than hexagonal (e.g., D-shaped, rectangular, oval, etc.) In addition, the spacer blocks may be used throughout different ranges of flexion. The set of surgical instruments may be used in conjunction with various methods for sensing pressure prior to implantation of a prosthetic knee joint such as that disclosed in U.S. Ser. No. 07/790,176. Various other alternatives and modifications may be made to the illustrative embodiment without departing from the spirit and scope of the invention.

What is claimed is:

1. A set of surgical instruments used for shaping a bone so as to receive a permanent component of a joint prosthesis having a smooth curvilinear surface, said set of surgical instruments comprising:

a provisional component having a surface corresponding to the smooth curvilinear surface of the permanent component of the joint prosthesis;

at least one resection guide operable to be used during resection of the bone;

an intramedullary rod assembly for adjustably positioning said one provisional component and said resection guide in order to shape the bone for receipt of the permanent component of the joint prosthesis, said intramedullary rod assembly including:
   (a) a first member operable to be inserted into the bone;
   (b) a second member moveable with respect to said first member of said intramedullary rod assembly; and means for adjusting the position of said second member relative said first member.

2. The set of surgical instruments according to claim 1, wherein said one component of said joint prosthesis has an articulating surface corresponding to said smooth curvilinear surface, said means for adjusting includes a provisional component having an articulating surface generally corresponding to said articulating surface of said one component of said joint prosthesis.

3. The set of surgical instruments according to claim 2, further comprising a support member being operable to be attached to said one resection guide and said provisional component, said support member being operable to be positioned within the bone and being operable to establish the valgus angle of the bone.

4. The set of surgical instruments of claim 2, wherein said means for positioning said one resection guide is further operable to adjustably position said articulating surface of said provisional component with respect to said bone.

5. The set of surgical instruments according to claim 1, wherein said first member has a bore of adjustable depth which is operable to control the position of said one resection guide.

6. The set of surgical instruments according to claim 1, wherein said includes:

first member comprises an intramedullary rod having a partially threaded bore, and said means for adjusting comprises a threaded member operable to engage said threaded portion of said bore of said intramedullary rod, the position of said threaded member within said bore being operable to determine the position of said one resection guide.

7. The set of surgical instruments according to claim 1, wherein said first member comprises an intramedullary rod operable to be at least partially disposed within said bone, and said second member comprises a support member operable to support said provisional component with respect to said intramedullary rod, said support member being further operable to support said one resection guide.

8. A set of surgical instruments used for shaping a femur so as to receive the femoral component of a knee joint prosthesis, said femoral component of said knee joint prosthesis having an articulating surface, said set of surgical instruments comprising:

a plurality of provisional components of different sizes, each of said provisional components having an articulating surface which generally corresponds to the articulating surface of said femoral component of said knee joint prosthesis;

means for adjusting the position of said provisional components with respect to said femur, said means for adjusting the position of said provisional components including:
   (a) a plurality of support members each of which have an angled surface generally corresponding to the possible valgus angles of said femur, and
   (b) each of said provisional components being operable to be secured to each of said support members; and means for guiding the resection of said femur in response to the position of said provisional component with respect to said femur.

9. The set of surgical instruments according to claim 8, wherein said means for adjusting the position of said provisional component with respect to said femur includes:

(a) an intramedullary rod operable to be disposed within said femur, said support members being operable to support said provisional components with respect to said intramedullary rod; and
   (b) means for adjustably positioning said support member with respect to said intramedullary rod.

10. The set of surgical instruments according to claim 9, wherein said means for adjustably positioning said support member with respect to said intramedullary rod includes a threaded member which is operable to engage said intramedullary rod, the position of said threaded member with respect to said intramedullary rod being operable to determine the position of at least one of said support members with respect to said intramedullary rod.

11. The set of surgical instruments according to claim 10, wherein said threaded member is operable to be secured to at least one of said support members.

12. The set of surgical instruments according to claim 10, wherein at least one of said support members are further operable to support and position said means for guiding the resection of said femur.

13. The set of surgical instruments according to claim 12, further comprising a plurality of resection guides each being operable to engage said support members.

14. The set of surgical instruments according to claim 13, further including a drill guide which is operable to be positioned by and receive support from at least one of said support members.

15. A method for preparing a first bone of a joint to receive a permanent component of a joint prosthesis having a smooth curvilinear surface, said method comprising the steps of:

providing a provisional component having a locating surface which is able to be adjustably positioned with respect to said first bone, said provisional component further having a surface corresponding to the smooth curvilinear surface of said permanent component;

adjusting the position of said locating surface on said provisional component so as to determine an adjusted position of said locating surface on said provisional component, said adjusting being performed in response to the provisional placement of said provisional component at a first portion of flexion of said joint, said step of adjusting the position of said locating surface including the steps of:

inserting an intramedullary rod into said first bone, said intramedullary rod including means for adjusting said locating surface, and adjusting said means for adjusting said locating surface to control the position of said locating surface;

resecting said first bone at a position determined at least in part by said adjusted position of said locating surface of said provisional component in order to prepare said first bone for receipt of said permanent component;

removing said provisional component; and installing said permanent component of said joint prosthesis on said first bone.

16. The method of claim 15, further comprising the additional step of selecting the size of said provisional component in response to the provisional placement of said provisional component at a second portion of flexion of said joint.

17. The method of claim 15, wherein said step of adjusting the position of a locating surface further comprises the additional steps of:

(a) establishing the position of said provisional component using said locating surface, (b) determining the space between said provisional component and a second bone at two portions of flexion of said joint, (c) readjusting the position of said locating surface until the space between said provisional component and said second bone is substantially the same at said two portions of flexion of said joint.

18. The method of claim 15, wherein said intramedullary rod includes a bore and said means for adjusting includes a threaded member and wherein said step of adjusting the position of a locating surface includes the step of:

(a) inserting said threaded member into said bore of said intramedullary rod thereby establishing said locating surface, and (b) rotating said threaded member to change the position of said locating surface.

19. The method of claim 15, wherein said intramedullary rod includes a bore and said means for adjusting includes a threaded member and wherein said step of adjusting the position of a locating surface includes the step of:

(a) inserting a support member into said bore of said intramedullary rod, (b) using said threaded member to adjustably position said support member within said intramedullary rod, (c) securing a provisional component to said support member, (d) adjusting the position of said provisional component by rotating said threaded member, (e) removing said provisional component from said support member, and (f) securing a plurality of cutting guides to said support member.

* * * * *